United States Patent [19]

Zhu et al.

[11] Patent Number: 5,069,766
[45] Date of Patent: Dec. 3, 1991

[54] SUPPRESSION OF ELECTROENDOSMOSIS IN CAPILLARY ELECTROPHORESIS

[75] Inventors: Ming-De Zhu, Berkeley; Roberto Rodriguez, Richmond; C. Timothy Wehr, Albany, all of Calif.

[73] Assignee: Bio-Rad Laboratories, Inc., Hercules, Calif.

[21] Appl. No.: 631,804

[22] Filed: Dec. 20, 1990

[51] Int. Cl.$^5$ .................. B01D 57/02; B01D 61/42
[52] U.S. Cl. .......................... 204/180.1; 204/182.9; 204/299 R
[58] Field of Search ............ 204/180.1, 295 R, 182.9

[56] References Cited

U.S. PATENT DOCUMENTS

4,312,739  1/1982  Hansson et al. .............. 204/182.9
4,931,328  6/1990  Swedberg ..................... 204/180.1

Primary Examiner—John Niebling
Assistant Examiner—Caroline Koestner
Attorney, Agent, or Firm—Townsend and Townsend

[57] ABSTRACT

Spontaneous and undesired electroendosmosis in a capillary during an electrophoretic separation procedure is suppressed by the inclusion of a viscosity-raising additive in one or both of the electrode chamber solutions. The additive is either a viscous water-soluble polymer, a hydrophilic gel, or a combination of the two.

27 Claims, 5 Drawing Sheets

SUPPRESSION OF ELECTROENDOSMOSIS IN CAPILLARY ELECTROPHORESIS

This invention lies in the field of gel-free capillary electrophoresis, and relates in particular to the spontaneous occurrence of electroendosmosis and its interference with electrophoretic separations.

BACKGROUND OF THE INVENTION

Capillary electrophoresis is a technique of considerable interest in the analysis of biological mixtures, particularly mixtures of small peptides, proteins and nucleic acids, since it can be used on extremely small samples and permits the use of high voltages which produce separations at high speed. Capillaries also offer the advantage of permitting on-line spectroscopic detection, a simple and highly efficient means of detection which avoids dilution of the solutes as well as any inaccuracies due to peak broadening or mixing upon emergence of the solutes from the capillary. Capillary electrophoresis in general encompasses various types of electrophoretic separations, most notably free zone electrophoresis and isoelectric focusing. Free zone electrophoresis is performed with a buffer solution as the separation medium. Solute separation and detection are performed in a single step as the solutes travel continuously at rates varying with their charge-to-mass ratio. The electric current thus serves both to separate the solutes into zones and to draw the zones in sequence across a detection point. Isoelectric focusing is performed in a medium containing a mixture of ampholytes with a pH gradient extending along the length of the capillary. In a focusing stage, the electric current causes each solute to travel until it reaches the location at which the pH is equal to the isoelectric point of the solute. The focusing stage is complete when all solutes are stabilized at their respective positions along the capillary, and this is followed by a mobilization stage in which the entire solute pattern is mobilized by any of various techniques toward or past a detection point.

A phenomenon which frequently occurs in capillary electrophoresis, particularly when the capillary is made of a silica-containing material, is electroendosmosis, also referred to as electroosmotic flow. Electroendosmosis arises from an electrokinetic potential existing between the wall of the solid element and the liquid separation medium adjacent to the wall. The flow which is caused by this potential is a bulk flow which occurs when an electric field tangential to the solid surface is imposed on the separation medium.

Bulk flow due to electroendosmosis has a potentially major effect in capillaries. Such bulk flow impairs the separation since it tends to cause mobilization of all solutes regardless of their electrophoretic mobility by mobilizing the separation medium itself, thereby interfering with the differentials in mobilization attributable to individual solute response. In extreme cases, this causes peak broadening and loss of resolution. Also, the electroendosmotic force varies from one run to the next as proteins become nonspecifically absorbed and desorbed at the capillary surface. This detracts from the reproducibility of the separation.

Electroendosmosis is commonly suppressed in capillaries by a coating on the interior capillary wall. The coating generally consists of neutral groups covalently bound to the capillary surface, eliminating any charged groups which are exposed and shielding the liquid medium adjacent to the wall from any charged groups remaining which are near the surface. In some cases, however, these coatings tend to deteriorate with extended use or with exposure to harsh solutes or separation media. This limits the useful life of capillaries and, when capillaries with partially deteriorated coatings are used in isoelectric focusing, the deterioration limits the length of the focusing time for any single run.

SUMMARY OF THE INVENTION

It has now been discovered that electroendosmosis in a capillary electrophoretic process can be suppressed by adding a viscosity-raising solute or gel to either the anolyte or catholyte or both. This may be achieved for example by dissolving a polymer or forming a gel in either or both of the two electrode solutions. When a polymer is used, the polymer will be of a character and in an amount sufficient to result in an increase in viscosity to the extent that bulk flow from the electrode chamber into the capillary interior, or vice versa, is reduced. When a gel is used, it will likewise be of sufficient concentration and density to prevent bulk flow from the electrode chamber into the capillary interior, or vice versa.

Electroendosmosis is suppressed without the use of a specially treated capillary, and without the need to place additional components inside the capillary which might interfere with the separation or impede the mobilization of the solutes. The invention has the further advantage of permitting longer focusing times in isoelectric focusing, and eliminating any loss of reproducibility due to deteriorating capillary coatings. Other features and advantages of the invention will become apparent from the description which follows.

DETAILED DESCRIPTION OF THE INVENTION AND PREFERRED EMBODIMENTS

While the invention may be practiced with viscosity-increasing additives simultaneously in both electrode chambers, i.e., anolyte and catholyte, effective results are also obtained using an additive in only one of the two chambers. The choice of chamber in relation to the direction which the electroendosmotic bulk flow would tend to occur is not critical; the additive may thus be placed in either the inlet end or the outlet end electrode chamber (in terms of the direction of electroendosmotic flow). In preferred embodiments, however, the additive is placed in the electrode chamber at the inlet end. With capillaries of silica-containing materials, for example, electroendosmotic flow tends to occur in the direction of the cathode. In the preferred practice of the invention for silica-containing capillaries, therefore, the additive is placed in the anolyte.

When a polymer is used, the polymer may be any polymer soluble in the electrolyte solution in which it is to be placed, which will increase the viscosity. Preferred polymers are those which are characterized as having a viscosity of at least about 50 centipoise as a 2% by weight aqueous solution at 25° C., preferably at least about 75 centipoise under these conditions, and most preferably at least about 100 centipoise under these conditions. Accordingly, the viscosity of the actual electrolyte solution with the polymer dissolved in it for use in the anolyte or catholyte chamber may vary widely, so long as it suppresses bulk flow into or out of the capillary to a sufficient extent to either substantially reduce or to substantially eliminate interference with the electrophoretic separation. The viscosity will generally be at a level higher than what could be introduced into the capillary itself. In most cases, best results will be obtained with solutions having a viscosity of at least about 50 centipoise, preferably at least about 100 centipoise, more preferably at least about 1000 centipoise, and most preferably at least about 2500 centipoise. The concentration of the polymer can vary and will be selected to achieve a solution of the desired viscosity. In most cases, the concentration will range from about 0.3% to about 10% on a weight basis, preferably from about 1% to about 5%.

Examples of polymers suitable for use in this invention are cellulose derivatives, polyalkylene glycols, saccharide-based and substituted saccharide-based polymers, polysilanes, polyacrylamide, polyvinylalcohol and polyvinylpyrrolidone. Examples of cellulose derivatives are sodium carboxymethyl cellulose, sodium carboxymethyl 2-hydroxyethyl cellulose, 2-hydroxyethyl cellulose, 2-hydroxypropyl cellulose, methyl cellulose, hydroxypropyl methyl cellulose, hydroxyethyl methyl cellulose, hydroxybutyl methyl cellulose, and hydroxyethyl ethyl cellulose. Examples of polyalkylene glycols are polyethylene and polypropylene glycols. Examples of saccharide-based and substituted saccharide-based polymers, both linear and branched, which are useful in the invention are dextran, hyaluronic acid (a polymer of acetylglucosamine and glucuronic acid as alternating units), locust-bean gum (a polysaccharide plant mucilage which is essentially galactomannan), Polytran (a scleroglucan available from Pillsbury Co., Minneapolis, Minnesota), Pustulan (a polysaccharide available from Calbiochem Corp., San Diego, California), amylose, amylopectin, soluble starch and hydroxylpropyl starch.

Gels suitable for use in this invention include any material which forms a gel in the electrolyte solution in which it is to be placed, and when so formed will impede or substantially reduce bulk flow into or out of the capillary. The gels may vary in terms of porosity, pore size, density, concentration, and chemical structure, including both naturally occurring and synthetic substances, none of which parameters are critical to the invention. Gels commonly used in as electrophoretic separation media as well as gels normally used for other purposes may all be used here. For aqueous systems, of course, the gel will be a hydrophilic gel. Notable among these are polyacrylamide gels and starch gels. Specific examples are gels of the Sephadex series and agarose gels. Combinations of gels, including different gel types, may also be used. Some of the most convenient gels for this use are polyacrylamide gels at concentrations of at least about 3% by weight, preferably from about 5% to about 10% by weight, and agarose gels at concentrations of from about 0.17% to about 8% by weight, preferably from about 0.5% to about 3% by weight.

The gel is preferably formed in situ in the electrode chamber itself. As for the physical connection between the electrode chamber and the capillary, a wide variety of configurations exist for capillary electrophoretic systems, with various types of connections. The optimum arrangement is one in which the gel is in direct contact with the opening of the capillary, or very close to it, minimizing any gaps or free volume between the two in which bulk flow can occur.

The term "incorporating" and similar terms are used herein to denote the means by which the additive is combined with the electrolyte solution. For soluble polymers, the term refers to "dissolving" a polymer in the electrolyte solution, while for gels, the term refers to "combining" the gel-forming colloid with the liquid solution in the known manner of gel formation. The actual means of incorporation is not critical, however, and further includes emulsions, suspensions and other types of mixtures. The only requirement is that the resulting electrolyte medium, be it solution, gel or otherwise, differ sufficiently from the fluid inside the capillary in terms of its resistance to bulk flow that the electrolyte medium offers resistance to any bulk flow tending to arise in the capillary without obstructing the passage of the electric current.

One advantage of the present invention is that the electrolyte solution containing the incorporated additive, be it dissolved polymer or gel, can be quickly and readily placed in the electrode chamber by the user, or exchanged or removed. This provides flexibility to the user in terms of permitting one to select at one's option a particular type and amount of dissolved polymer or gel to suit a particular system or separation, and to change it at will.

The present invention is applicable to capillaries of any materials which are susceptible to the formation of an electrokinetic potential. Such materials are those with polar groups at the surface, and particularly groups susceptible to ionization upon contact with an electrolyte solution. The degree of ionization as well as the polarity of the charge, and thus the direction of electroendosmotic flow (i.e., toward the anode or cathode), will vary with the material. The most common materials for capillary electrophoresis are silica-containing materials, for which as indicated above the direction of electroendosmosis is toward the cathode. Notable among silica-containing materials are glass, quartz and fused silica.

The size of the capillary in terms of both length and internal diameter are not critical, and the invention extends to a wide range of each. A higher degree of flow resistance in the electrode chamber will generally be required for wider capillaries, however. With this in mind, the appropriate selection in any given system is readily determinable by routine experimentation if not readily apparent to the skilled user. Capillaries will generally range from about 10 to about 200 microns in internal diameter, with about 20 to about 100 microns preferred. Capillaries with diameters at the lower end of these ranges will generally have a higher susceptibility to electroendosmosis, but will require lower concentrations of gel or dissolved polymer. Capillaries with diameters at the high end of these ranges will require higher concentrations of gel or dissolved polymer for equivalent results.

While the invention may be used as the sole means of suppressing electroendosmosis, it may also serve as a supplemental means. Thus, it may be used with coated capillaries whose coating reduces protein adsorption and also serves to suppress electroendosmosis. In such cases, the incorporation of the additive into either or both of the electrolyte chambers further suppresses the tendency toward electroendosmosis, and maintains the suppression as the coating ages, decomposes or dissolves, thereby extending the useful life of the capillary. The invention is particularly useful, however in uncoated capillaries in which the silanol groups are exposed to the liquid separation medium in the capillary.

This invention is applicable to all types of capillary electrophoresis, including both free zone electrophoresis and isoelectric focusing. In free zone electrophoresis, solutes migrate at differential velocities through the capillary under the influence of the electric field, and will continue to migrate while the field is imposed. The separation which is achieved is thus based on the differentials of migration velocity. The separation medium in the capillary may be a simple solution or a solution supplemented with a sieving agent or other additive selected to enhance the separation and resolution of the zones as they separate and travel along the length of the capillary. The solutions in the anode chamber and the cathode chamber are generally identical and at the same pH.

Free zone electrophoresis may also be combined with size exclusion or sieving to enhance the separation. This application of the invention thus includes separations which include a sieving agent such as an appropriate polymer in the capillary. This is particularly useful in the separation of mixtures which have identical or nearly identical charge-to-mass ratios, such as nucleic acids.

In isoelectric focusing, a pH gradient is established in the capillary by the use of an acidic solution in the anolyte and a basic solution in the catholyte, as well as the inclusion of a mixture of ampholytes in the separation medium in the capillary to form the pH gradient. Each solute migrates under the influence of the electric field to a position in the capillary where the pH is equal to the solute's isoelectric point. The separation, i.e., isoelectric focusing, is thus achieved on the basis of isoelectric points rather than differential mobilization velocities. Once focusing is complete, the pH gradient is shifted or displaced by changing one of the solutions or adding a species to it, and the solute zones are mobilized at uniform rates toward either the anolyte or the catholyte for purposes of detection. The present invention has utility in both the focusing and mobilization stages, but will be of greatest importance and influence during the focusing stage.

The following examples are offered by way of illustration, and are intended neither to limit nor to define the invention in any manner.

EXAMPLE 1

This example demonstrates the suppression of electroendosmotic flow in free zone electrophoresis in accordance with the invention, by use of an anolyte containing a viscous linear polymer, and also by use of an anolyte containing a combination of a gel and a viscous linear polymer. A simple anolyte solution is also included for comparison.

In each run in this example, two vitamins were separated in an uncoated capillary using positive to negative polarity under alkaline pH conditions. Niacinamide is an uncharged vitamin which migrates in the capillary only under the influence of electroendosmosis. Thiamine is a cationic vitamin whose migration is due to the combined effects of electroendosmosis and its inherent electrophoretic mobility (which under these conditions is in the same direction as electroendosmosis). All separations were done under the following conditions:

capillary: 35cm $\times$ 50$\mu$m i.d., uncoated
separation medium: 10 mM sodium borate, pH 8.5
catholyte: 10 mM sodium borate, pH 8.5
load conditions: electrokinetic loading under constant voltage at 12kV for 4 seconds
run conditions: constant voltage at 10kV
detection: absorbance at 200 nm, 0.1 absorbance units full scale
sample: thiamine (1.25 mg/mL) +niacinamide (0.25 mg/mL) in 10 mM sodium borate, pH 8.5

Figure 1:
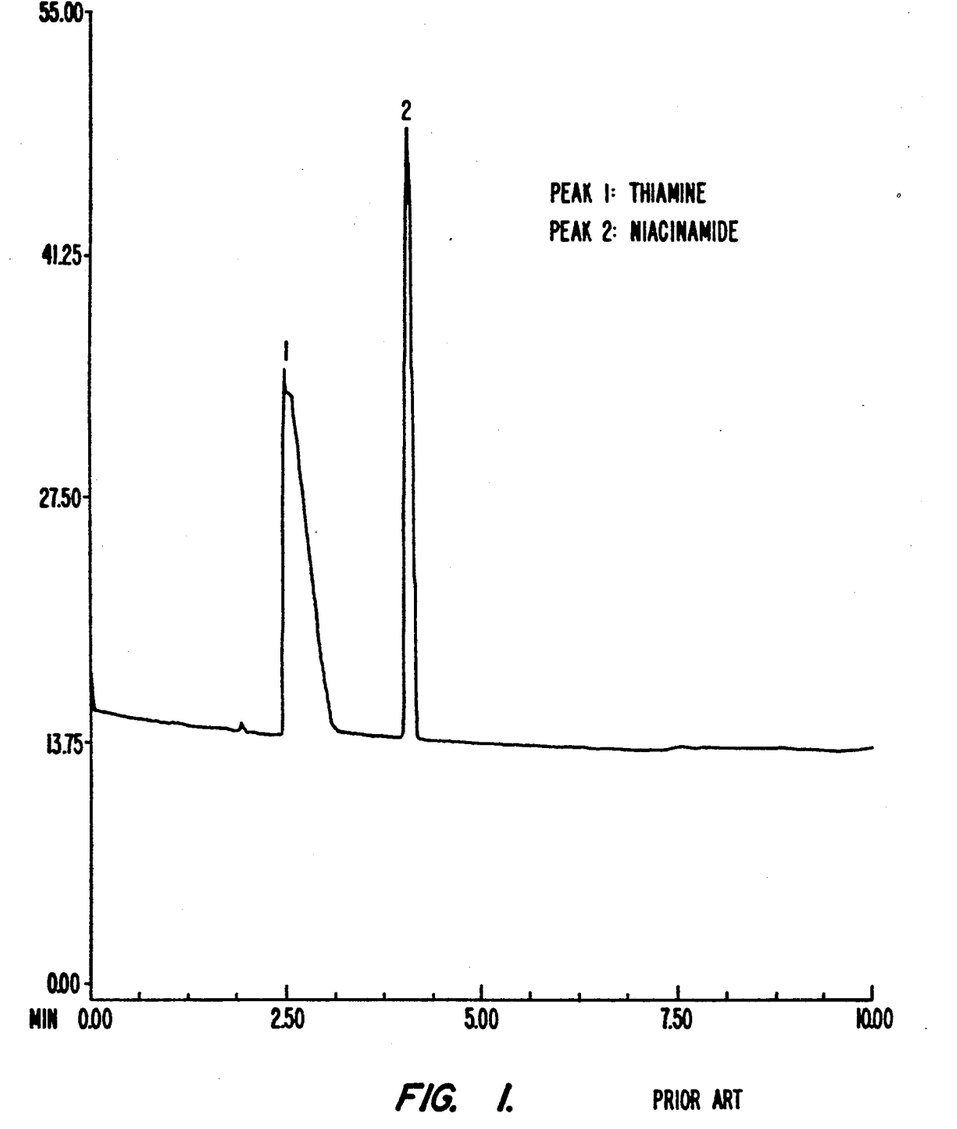
FIGS. 1, 2 and 3 are representations of detector traces from free zone electrophoresis experiments utilizing an example of the electroendosmosis suppression techniques of the present invention with an uncoated silica capillary. The three experiments were identical except that no electroendosmosis suppressing agent was used in FIG. 1, a linear viscous polymer was used as an electroendosmosis suppressing agent in FIG. 2, and a combination of a linear viscous polymer and a gel were used in FIG. 3.

FIG. 1 shows the separation of thiamine and niacinamide in the uncoated capillary using 10 mM sodium borate (pH 8.5) as the anolyte, i.e., no electroendosmosis suppressing agent present—for comparison purposes outside the scope of the present invention. Using niacinamide as a marker for electroendosmosis, the electroendosmotic mobility ($\mu_{EEO}$) is calculated to be $9.66 \times 10^{-4}$ cm$^2$sec$^{-1}$V$^{-1}$. The asymmetry of the thiamine peak in this Figure as well as FIGS. 2 and 3 is presumed to be due to the interaction of the vitamin with the capillary wall.

Figure 2:
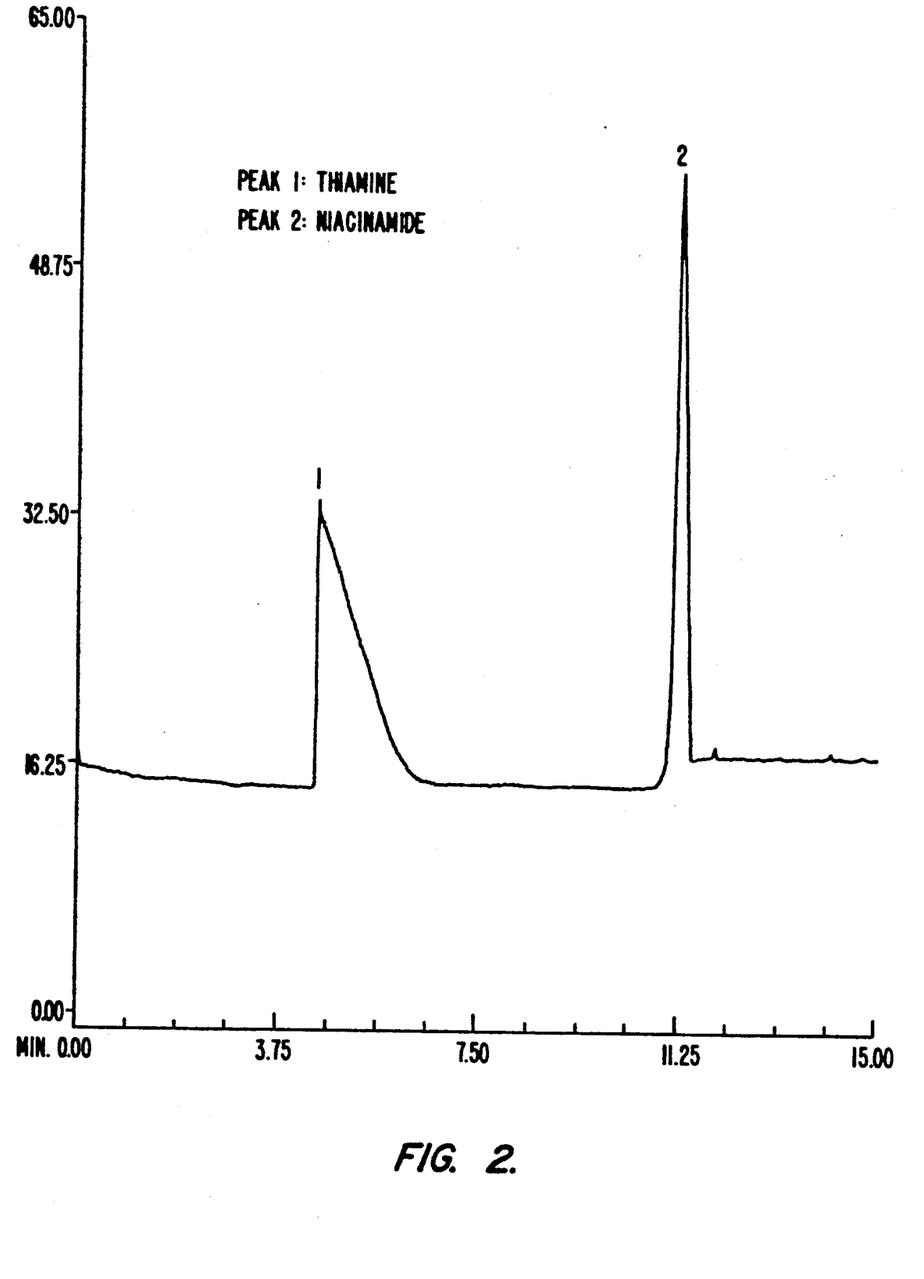

FIG. 2 shows the separation of the two vitamins in the uncoated capillary using an anolyte containing 10 mM sodium borate (pH 8.5) +1.8% hydroxypropylmethylcellulose (of which the viscosity of a 2% solution is 4000 centipoise). FIG. 2 thus shows that under these conditions, $\mu_{EEO}$ is reduced to $3.33 \times 10^{-4}$ cm$^2$sec$^{-1}$V$^{-1}$.

Figure 3:
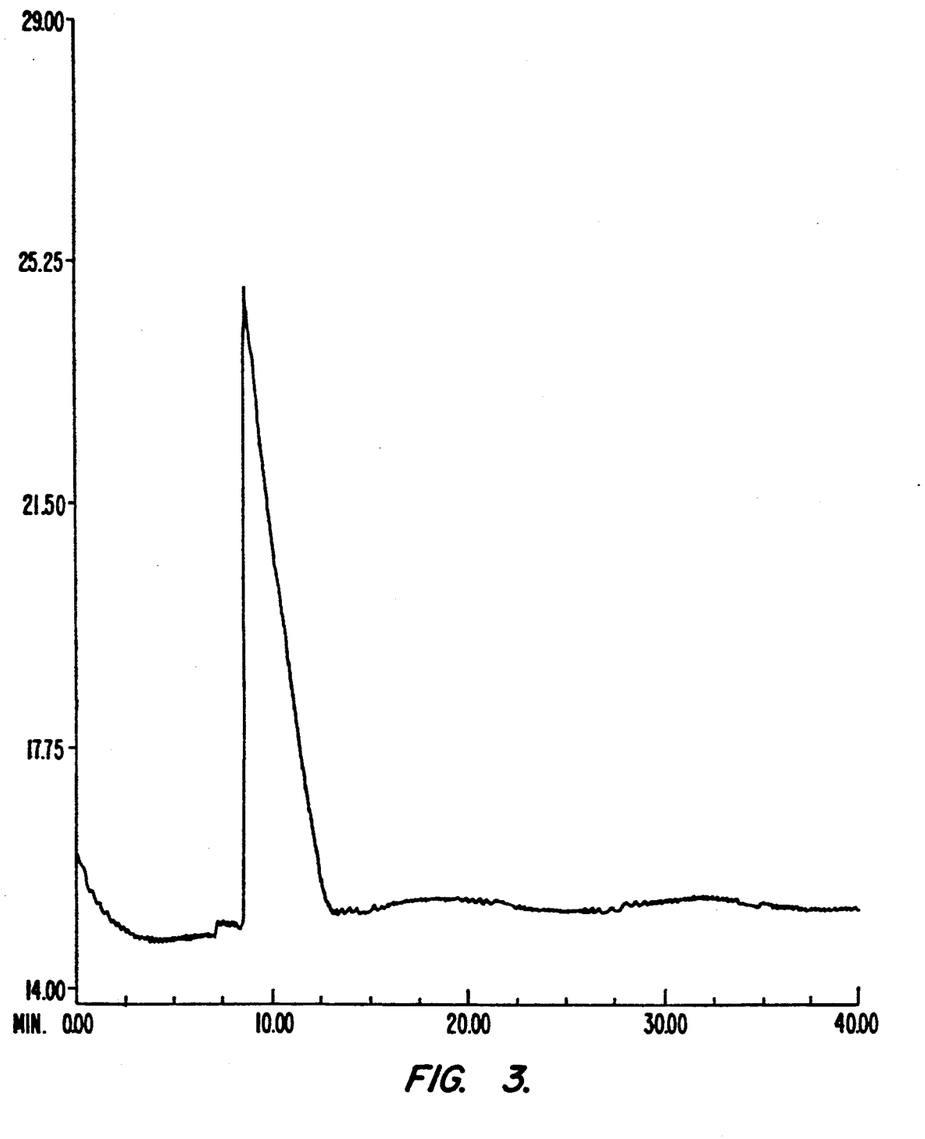

FIG. 3 shows the separation of the two vitamins in the uncoated capillary using an anolyte containing 10 mM sodium borate (pH 8.5) +1% zero-charge agarose +5% polyvinylalcohol (50,000 $M_r$). FIG. 3 thus shows that under these conditions, niacinamide does not elute within 40 minutes, indicating that $\mu_{EEO}$ is reduced to less than $0.9 \times 10^{-4}$ cm$^2$sec$^{-1}$V$^{-1}$.

To summarize, these comparisons show that the addition of a linear viscous polymer to the anolyte reduced electroendosmosis by at least 65%, and that addition of both a linear viscous polymer and a gel to the anolyte reduced electroendosmosis by at least 90%.

EXAMPLE 2

This example demonstrates that the addition of a viscous linear polymer to the anolyte suppresses the level of electroendosmotic flow in isoelectric focusing sufficiently to permit the formation of narrow focused zones. The sample used was a mixture of four hemoglobin variants, hemoglobins A, F, S and C. During the mobilization step, these variants migrate in this order. The experiments demonstrate that resolution of these four hemoglobin variants is considerably improved using an electroendosmosis suppressing agent in accordance with the present invention, and is comparable to that achieved using a coated capillary for the same purpose.

Figure 4:
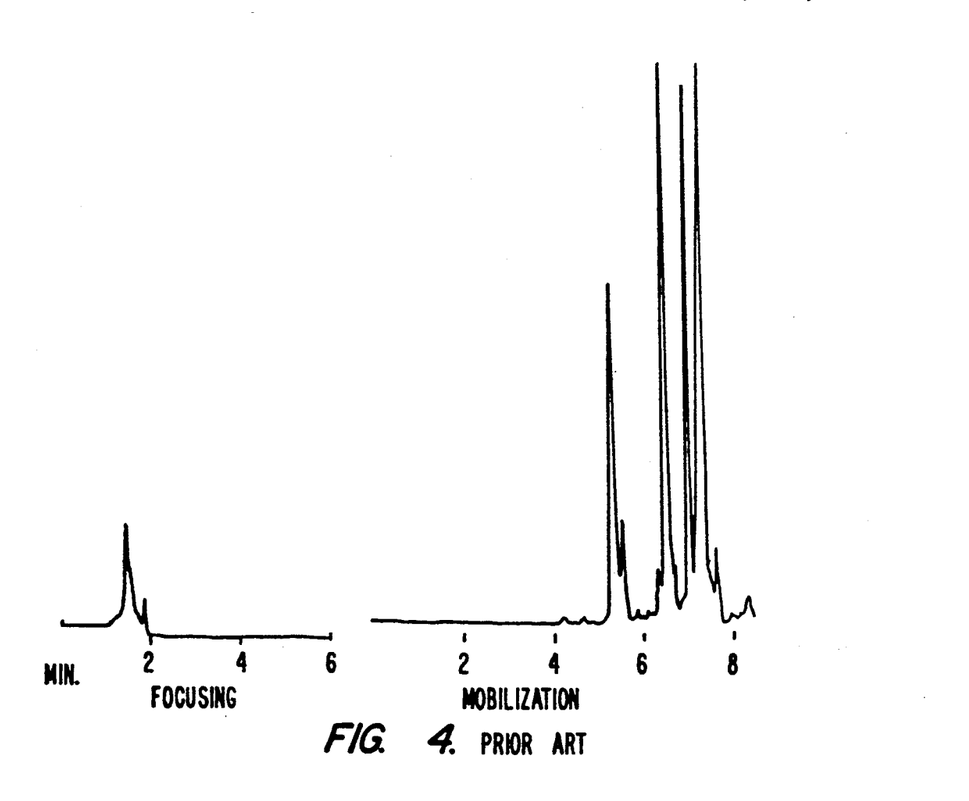
FIGS. 4, 5 and 6 are representations of detector traces from isoelectric focusing experiments in coated and uncoated capillaries. The coated capillary in FIG. 4 represents a prior art method of suppressing electroendosmosis; the uncoated capillary of FIG. 5 was used without an electroendosmosis suppressing agent, and the uncoated capillary in FIG. 6 was used with a viscous polymer as the electroendosmosis suppressing agent. All other conditions were identical among the three experiments.

Separations were performed under the following conditions:

capillary: 14 cm ×25 μm i.d., coated or uncoated as indicated catholyte: 20 mM sodium hydroxide mobilizing agent: 20 mM sodium hydroxide +80 mM sodium chloride sample: hemoglobins A, F, S and C (4 mg/mL total protein) in 2% Biolyte 3-10 focusing conditions: 7kV for 6 minutes mobilization conditions: 8kV detection: absorbance at 280 nm, 0.128 absorbance units full scale For FIG. 4, a coated capillary was used, with an anolyte containing only 40 mM phosphoric acid (no electroendosmosis suppressing agent)—a comparison test outside the scope of the present invention.

Figure 5:
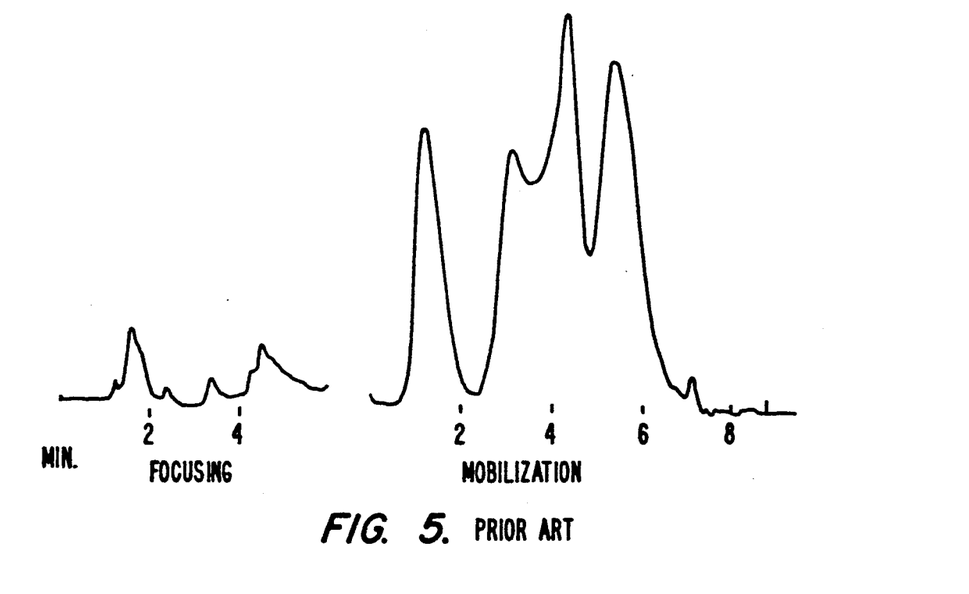

For FIG. 5, an uncoated capillary was used, and the anolyte again contained only 40 mM phosphoric acid (no electroendosmosis suppressing agent)—a comparison test outside the scope of the present invention.

Figure 6:
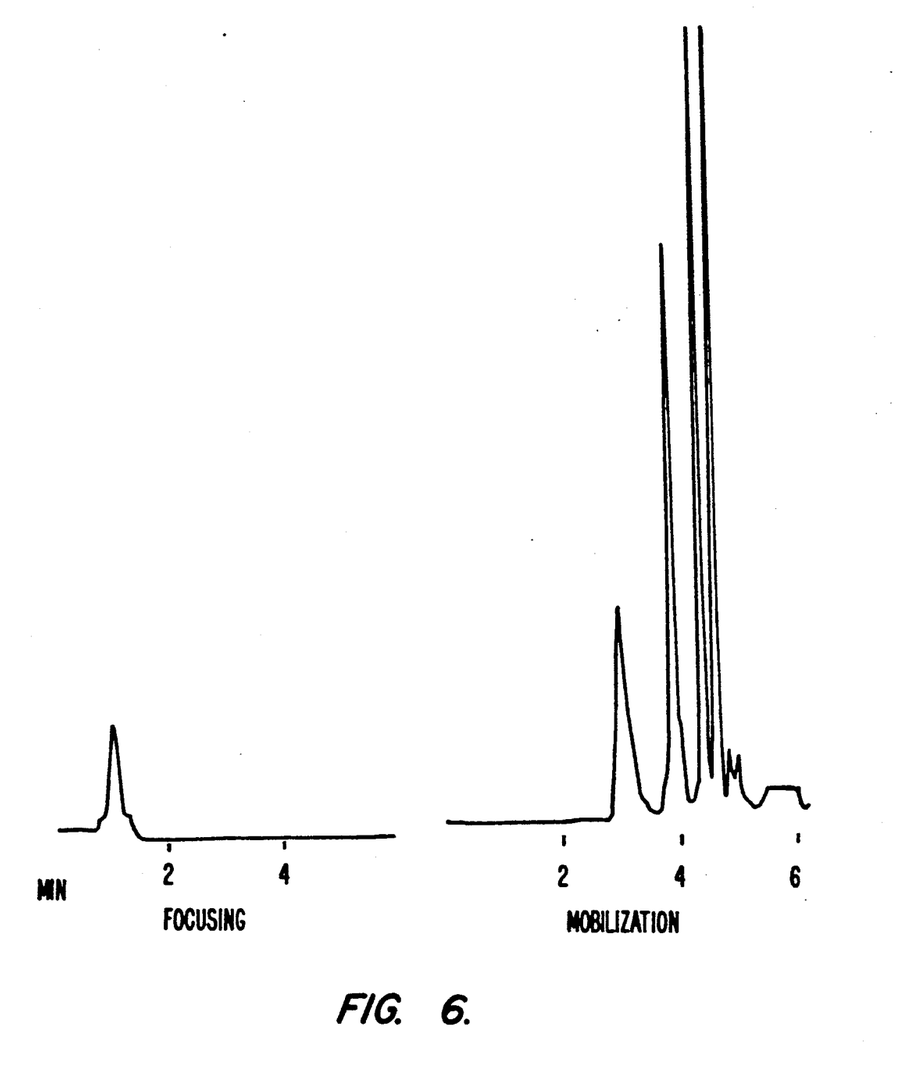

For FIG. 6, an uncoated capillary was used, and the anolyte this time contained 2% hydroxypropylmethylcellulose (4000 centipoise) as an electroendosmosis suppressing agent, in addition to the 40 mM phosphoric acid.

To summarize, these comparisons show the uncoated capillary with the polymer dissolved in the anolyte to be at least equivalent to the coated capillary in terms of electroendosmotic flow suppression.

The foregoing is offered primarily for purposes of illustration. It will be readily apparent to those skilled in the art that the methods, materials and system parameters may be further varied beyond what is described herein without departing from the spirit and scope of the invention.

What is claimed is:

1. A method for suppressing electroendosmosis during the electrophoretic separation of a liquid sample mixture into components in a capillary of a material susceptible to the formation of an electrokinetic potential, said capillary positioned in an electric current path between two electrolyte solutions containing a catholyte and anolyte, respectively, said method comprising incorporating an additive selected from the group consisting of a water-soluble polymer, a hydrophilic gel, and a combination thereof into one or both of said electrolyte solutions, in sufficient quantity to resist bulk flow through the end of said capillary opening therein.

2. A method in accordance with claim 1 in which said capillary is of a silica-containing material.

3. A method in accordance with claim 1 in which said capillary is of a silica-containing material selected from the group consisting of glass, quartz and fused silica.

4. A method in accordance with claim 1 in which said capillary is of a silica-containing material selected from the group consisting of glass, quartz and fused silica, without electroendosmosis-suppressing neutral organic groups bonded to the inner surface thereof.

5. A method in accordance with claim 1 in which said incorporated quantity of said additive is sufficient to raise the viscosity of the electrolyte solution in which said additive is incorporated to at least about 50 centipoise.

6. A method in accordance with claim 1 in which said incorporated quantity of said additive is sufficient to raise the viscosity of the electrolyte solution in which said additive is incorporated to at least about 1000 centipoise.

7. A method in accordance with claim 1 in which said incorporated quantity of said additive is sufficient to raise the viscosity of the electrolyte solution in which said additive is incorporated to at least about 2500 centipoise.

8. A method in accordance with claim 1 in which said additive is a polyacrylamide gel at a concentration of at least about 3% by weight.

9. A method in accordance with claim 1 in which said additive is a polyacrylamide gel at a concentration of from about 5% to about 10% by weight.

10. A method in accordance with claim 1 in which said additive is an agarose gel at a concentration of from about 0.17% to about 8% by weight.

11. A method in accordance with claim 1 in which said additive is an agarose gel at a concentration of from about 0.5% to about 3% by weight.

12. A method in accordance with claim 1 in which said additive is a water-soluble polymer selected from the group consisting of cellulose derivatives, polyalkylene glycols, saccharide-based and substituted saccharide-based polymers, polysilanes, polyacrylamide, polyvinylalcohol and polyvinylpyrrolidone.

13. A method in accordance with claim 1 in which said additive is a water-soluble polymer at a concentration sufficient to raise the viscosity of the electrolyte solution in which said additive is incorporated to at least about 50 centipoise.

14. A method in accordance with claim 1 in which said additive is a water-soluble polymer at a concentration sufficient to raise the viscosity of the electrolyte solution in which said additive is incorporated to at least about 1000 centipoise.

15. A method in accordance with claim 1 in which said additive is a combination of a water-soluble polymer at a concentration of from about 0.3% to about 10% by weight, and a hydrophilic gel at a concentration of at least about 1% by weight.

16. A method in accordance with claim 1 in which said additive is a combination of a water-soluble polymer at a concentration of from about 1% to about 5% by weight, and a hydrophilic gel at a concentration of from about 3% to about 10% by weight.

17. A method in accordance with claim 1 in which said additive is a water-soluble polymer at a concentration sufficient to raise the viscosity of the electrolyte solution in which said additive is incorporated to at least about 2500 centipoise.

18. A method in accordance with claim 1 in which said additive is incorporated into only one of said electrolyte solutions.

19. A method in accordance with claim 1 in which said capillary is of a silica-containing material, and said additive is incorporated into said electrolyte solution containing said anolyte.

20. A method for suppressing electroendosmosis during the electrophoretic separation of a liquid sample mixture into components in a capillary of silica-containing material which does not contain electroendosmosis-suppressing neutral organic groups bonded to the inner surface thereof, said capillary positioned in an electric current path between a catholyte and an anolyte, respectively, said method comprising dissolving a water-soluble polymer into said anolyte in sufficient quantity to raise the viscosity of said anolyte to at least about 2500 centipoise.

21. A method for separating a liquid sample mixture into components by electrophoretic means without substantial interference due to electroendosmosis, in a capillary of a material susceptible to the formation of an electrokinetic potential, whose two ends open into electrolyte solutions containing a catholyte and anolyte, respectively, said method comprising passing an electric current through said capillary with an additive selected from the group consisting of a water-soluble polymer and a hydrophilic gel incorporated into one or both of said electrolyte solutions, in sufficient quantity to resist bulk flow through the end of said capillary opening therein.

22. A method in accordance with claim 21 in which said capillary is of a silica-containing material selected from the group consisting of glass, quartz and fused silica.

23. A method in accordance with claim 21 in which said capillary is of a silica-containing material selected from the group consisting of glass, quartz and fused silica, without electroendosmosis-suppressing neutral organic groups bonded to the inner surface thereof.

24. A method in accordance with claim 21 in which said additive is a water-soluble polymer selected from the group consisting of cellulose derivatives, saccharide-based and substituted saccharide-based polymers, polysilanes, polyvinylalcohol and polyvinylpyrrolidone.

25. A method in accordance with claim 21 in which said additive is a water-soluble polymer at a concentration sufficient to raise the viscosity of the electrolyte solution in which said additive is incorporated to at least about 1000 centipoise.

26. A method in accordance with claim 21 in which said additive is a water-soluble polymer at a concentration sufficient to raise the viscosity of the electrolyte solution in which said additive is incorporated to at least about 2500 centipoise.

27. A method in accordance with claim 21 in which said additive is incorporated into said anolyte only.

* * * * *